US00PP10127P

United States Patent [19]

Zaiger et al.

[11] Patent Number: Plant 10,127

[45] Date of Patent: Nov. 25, 1997

[54] PEACH TREE "GAYLA RICH"

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 676,919

[22] Filed: Jul. 8, 1996

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach *Prunus persica*, tree which has the unique combination of desirable features that are outstanding in a new variety:

1. Early maturity of large size fruit.
2. Heavy and regular production of fruit.
3. Fruit with firm flesh, good flavor and eating quality.
4. Fruit with a high degree of attractive red skin color.
5. Fruit with good handling and shipping quality.
6. Coloring of the fruit 5 to 6 days before maturity.
7. Vigorous, upright growth of tree.

1 Drawing Sheet

ORIGIN OF THE VARIETY.

The present new and distinct variety of peach tree was developed by us in our experimental orchard located near Modesto, Calif., as a first generation cross between Earlirich Peach (U.S. Plant Pat. No. 9,002) and a selected seedling (field identification number 104LB628). The paternal parent (104LB628), originated from a third generation cross between an open pollinated seedling of May Grand Nectarine (U.S. Plant Pat. No. 2,794), crossed with May Crest Peach (U.S. Plant Pat. No. 4,064). We grew and maintained a large group of these first generation seedlings under close and careful observation, during which time, one such seedling, which is of the present variety, exhibited the distinctive desirable fruit characteristics described above and was selected for asexual reproduction and commercialization.

ASEXUAL REPRODUCTION OF THE VARIETY

The new and distinct variety of peach tree was asexually propagated by budding, as performed by us in our experimental orchard located near Modesto, California, and shows that all characteristics of the tree and its fruit are established and transmitted through succeeding asexual propagations and come true to the original tree in all respects.

SUMMARY OF THE VARIETY.

The herein described variety of peach tree is of large size, vigorous, upright growth and a productive and regular bearer of large, firm, yellow flesh, clingstone fruit with good handling and shipping quality. The fruit is further characterized by having good flavor and eating quality, having a high degree of attractive red skin color and ripening in the early maturity season. In comparison to the early maturing May Crest Peach (U.S. Plant Pat. No. 4,064), the new variety has greater production of larger, more uniform size fruit with a higher degree of attractive red skin color and ripening in the same maturity season.

DESCRIPTION OF THE PHOTOGRAPH.

The accompanying photographic illustration shows typical specimens of the foliage and fruit of the present new variety of peach tree. The upper and lower surface of the leaves being illustrated, the exterior and a sectional view of the fruit being divided in the suture plane to reveal flesh coloration, pit cavity and a stone remaining in place. The photograph of the fruit was taken shortly after being picked at maturity (firm ripe) and the colors are as nearly true as is reasonably possible in a color representation of this type.

DESCRIPTION OF THE VARIETY.

The following is a detailed botanical description of the flowers, foliage and fruit of the present new peach variety, as based on observation of the variety grown in our experimental orchard located near Modesto, California, with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium.
- *Shape.*—Usually pruned to vase shape.
- *Productivity.*—Productive.
- *Bearer.*—Regular.

Trunk:
- *Size.*—Medium stocky.
- *Texture.*—Medium shaggy.
- *Color.*—Brown to grayish brown (5-E-4) to (5-E-5).

Branches:
- *Size.*—Medium.
- *Texture.*—Smooth to medium rough.
- *Lenticals.*—Numerous. Medium to large size.
- *Color.*—Light reddish brown to brown (5-D-4) to (5D-6). Varies with age of growth.

Leaves:
- *Size.*—Large. Average length—6". Average width—1½".
- *Form.*—Lanceolate, pointed.
- *Texture.*—Smooth.
- *Thickness.*Medium.
- *Color.*—Upper surface green to deep green (28-E-5) to (28-E-8). Lower surface dull green to green (28-D-4) to (28-D-7).
- *Margin.*—Crenate.
- *Petiole.*—Short to medium length. Medium thickness.
- *Glands.*—Reniform. Number varies from 1 to 3. Average number 2. Small to medium size. Positioned on lower portion of leaf blade and upper portion of petiole.

Flower buds:
*Size.*—Medium.
*Form.*—Plump.
*Pubescence.*—Pubescent.
Flowers:
*Size.*—Large, showy.
*Blooming period.*—Date of first bloom: Feb. 26, 1994. Date of last bloom: Mar. 3, 1994. Varies slightly with climatic conditions.
*Pollen.*—Present, self-fertile.
*Color.*—Pink.
Fruit:
*Maturity when described.*—Firm ripe.
*Date of first picking.*—May 20, 1994.
*Date of last picking.*—May 26, 1994.
*Size.*—Large Average diameter axially 2¾". Averge transversely in suture plane 2¾".
*Form.*—Nearly globose, slightly flattened at stem end.
*Suture.*—Shallow, extends from base to apex.
*Ventral surface.*—Nearly round, some fruit slightly lipped.
*Cavity.*—Rounded to slightly elongated in suture plane. Average depth—⅜". Average breadth—¾".
*Base.*—Retuse.
*Apex.*—Usually slight apical point, varies from slight apical point to rounded.
Flesh:
*Ripens.*—Relatively even, only slightly earlier near apex.
*Texture.*—Firm.
*Juice.*—Moderate.
*Aroma.*—Moderate.
*Amygdalin.*—Undetected.
*Flavor.*—Good, good balance between sugar and acid.
*Eatin quality.*—Good.
*Fibers.*—Few, small, tender.
*Color.*—Light yellow to yellow (3-A-4) to (3-A-6). Pit cavity—yellow to light grayish yellow (3-A-5) to (3-B-4).
Skin:
*Thickness.*—Medium.
*Texture.*—Medium, tenacious to flesh.
*Tendency to crack.*—None.
*Down.*—Moderate, short in length.
*Color.*—Yellow to golden yellow ground color (4-A-5) to (5-A-4). Nearly overspread with red to madder red (10-B-7) to (10-D-7).
Stone:
*Type.*—Clingstone.
*Size.*—Large. Average length—1⅜". Average width —1 1/16". Average thickness—⅝".
*Form.*—Oval to obovate.
*Base.*—Usually rounded, varies from straight to rounded.
*Apex.*—Usually rounded, varies from rounded to acuminate.
*Surface.*—Irregularly furrowed toward apex, pitted throughout, pit cavities vary from round to elongated.
*Ridges.*—Usually rounded.
*Sides.*—Equal to unequal.
*Tendency to split.*—Slight.
*Color.*—Light tan to light brown (5-B-4) to (5-D-4).
Use: Dessert.
*Market.*—Local and long distance.
Keeping quality: Good.
Shipping quality: Good.

The new and distinct variety of peach tree, its flowers, foliage and fruit may vary in slight detail due to climate, soil conditions and cultural practices under which the variety may be grown, the present description is that of the variety grown under the ecological conditions prevailing near Modesto, Calif.

We claim:

1. A new and distinct variety of peach tree, substantially as illustrated and described, characterized by its large size, vigorous, upright growth and a productive and regular bearer of large, firm, yellow flesh, clingstone fruit with good flavor and eating quality; the fruit is further characterized by having a high degree of attractive red skin color, having firm flesh with good handling and shipping quality, and in comparison to the early maturing May Crest Peach (U.S. Plant Pat. No. 4,064), the new variety matures in the same maturity season with greater production of larger size fruit.

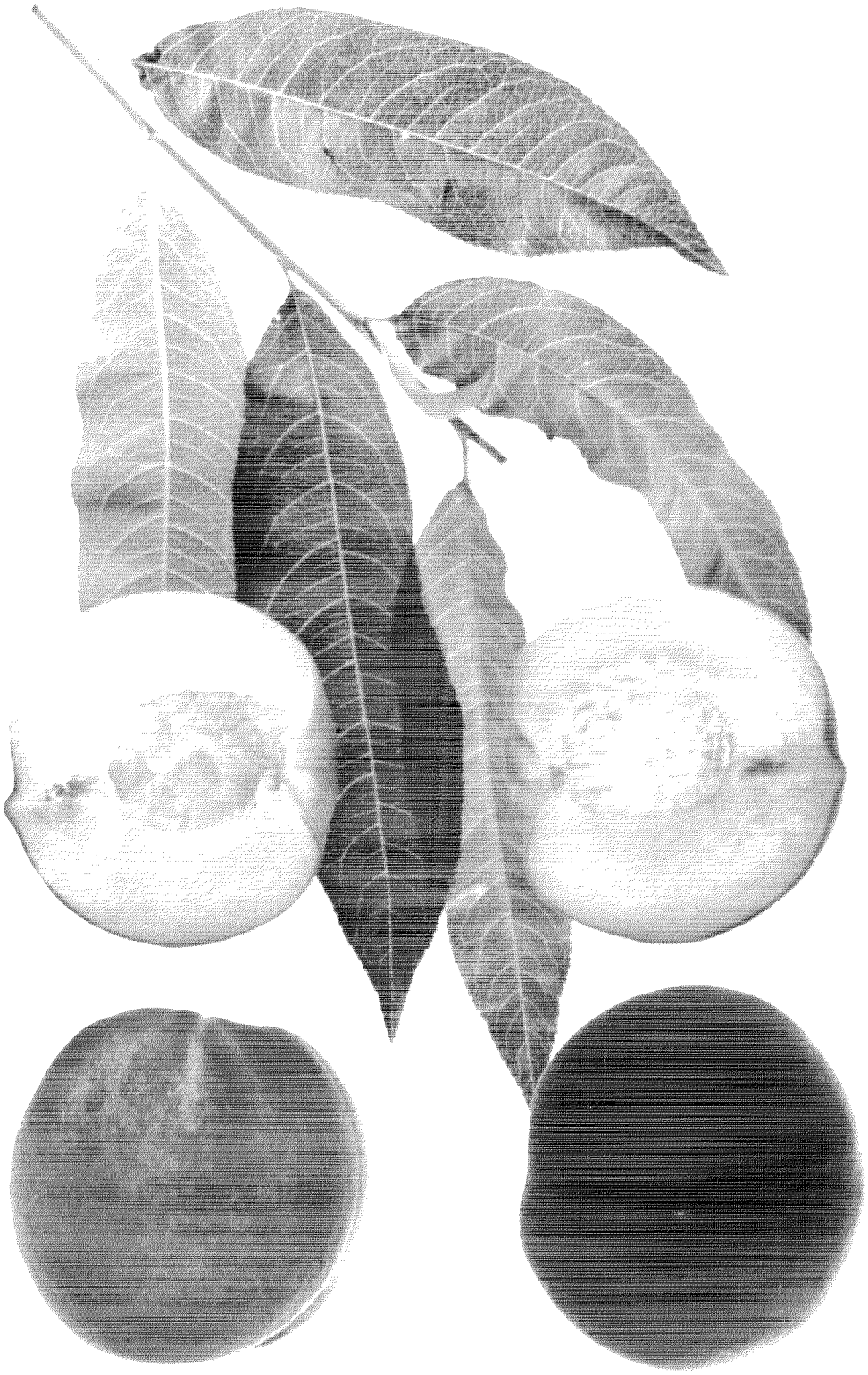

* * * * *